United States Patent
Johnson

(10) Patent No.: US 11,944,582 B2
(45) Date of Patent: Apr. 2, 2024

(54) COMPRESSION DEPTH MONITOR WITH VARIABLE RELEASE VELOCITY FEEDBACK

(71) Applicant: ZOLL Medical Corporation, Chelmsford, MA (US)

(72) Inventor: Guy R Johnson, Wilton, NH (US)

(73) Assignee: ZOLL Medical Corporation, Chelmsford, MA (US)

( * ) Notice: Subject to any disclaimer, the term of this patent is extended or adjusted under 35 U.S.C. 154(b) by 741 days.

(21) Appl. No.: 16/167,573

(22) Filed: Oct. 23, 2018

(65) Prior Publication Data
US 2019/0053976 A1  Feb. 21, 2019

Related U.S. Application Data

(63) Continuation of application No. 13/874,372, filed on Apr. 30, 2013, now abandoned.

(51) Int. Cl.
*A61H 31/00* (2006.01)
*A61N 1/39* (2006.01)

(52) U.S. Cl.
CPC ......... *A61H 31/005* (2013.01); *A61H 31/007* (2013.01); *A61H 2201/5007* (2013.01);
(Continued)

(58) Field of Classification Search
CPC .............. A61H 31/00; A61H 2031/001; A61H 2031/002; A61H 2031/003; A61H 31/004;
(Continued)

(56) References Cited

U.S. PATENT DOCUMENTS 3,513,850 A  5/1970  Weber
3,865,101 A  2/1975  Saper et al.
(Continued)

FOREIGN PATENT DOCUMENTS

CN  1058538  2/1992
CN  1146319  4/1997
(Continued)

OTHER PUBLICATIONS

Marc D. Berg, "Part 13 Pediatric Basic Life Support", 2010 American Heart Association Guidelines for Cardiopulmonary Resuscitation and Emergency Cardiovascular Care, Nov. 2, 2010.*
(Continued)

*Primary Examiner* — Tu A Vo
(74) *Attorney, Agent, or Firm* — The Webb Law Firm

(57) ABSTRACT

A system for providing cardiopulmonary resuscitation (CPR) feedback configurable at a point of use is described that includes one or more sensors configured to generate a signal corresponding to motion of the chest during an administration of chest compressions and a defibrillator configured to couple to the one or more sensors, the defibrillator including an input device configured to accept user input indicative of a compression depth goal, one or more processors and a memory, the one or more processors configured to determine chest compression feedback that varies based on the user input and is based at least in part on the motion of the chest during the administration of chest compressions, and a display configured to display the chest compression feedback.

15 Claims, 6 Drawing Sheets

(52) U.S. Cl.
CPC .............. *A61H 2201/5043* (2013.01); *A61H 2201/5064* (2013.01); *A61H 2201/5079* (2013.01); *A61H 2201/5084* (2013.01); *A61H 2201/5092* (2013.01); *A61N 1/3993* (2013.01)

(58) Field of Classification Search
CPC .............. A61H 31/007; A61H 31/008; A61H 2201/1619; A61H 2203/0456; A61H 2205/08; A61H 2205/084; A61H 2201/5058; A61H 2201/5061; A61H 2201/5064; A61H 2201/5079; A61H 2201/5084; A61H 2201/50
See application file for complete search history.

(56) References Cited

U.S. PATENT DOCUMENTS

| | | |
|---|---|---|
| 4,019,501 A | 4/1977 | Harris |
| 4,077,400 A | 3/1978 | Harrigan |
| 4,088,138 A | 5/1978 | Diack et al. |
| 4,095,590 A | 6/1978 | Harrigan |
| 4,193,064 A | 3/1980 | Snyder |
| 4,198,963 A | 4/1980 | Barkalow et al. |
| 4,198,964 A | 4/1980 | Honneffer |
| RE30,372 E | 8/1980 | Mirowski et al. |
| 4,273,114 A | 6/1981 | Barkalow et al. |
| 4,326,507 A | 4/1982 | Barkalow |
| 4,360,345 A | 11/1982 | Hon |
| 4,491,423 A | 1/1985 | Cohen |
| 4,588,383 A | 5/1986 | Parker et al. |
| 4,610,254 A | 9/1986 | Morgan et al. |
| 4,619,265 A | 10/1986 | Morgan et al. |
| 4,757,821 A | 7/1988 | Snyder |
| 4,797,104 A | 1/1989 | Laerdal et al. |
| 4,863,385 A | 9/1989 | Pierce |
| 4,928,674 A | 5/1990 | Halperin et al. |
| 4,932,879 A | 6/1990 | Ingenito et al. |
| 4,994,015 A | 2/1991 | Cadwell |
| 5,081,993 A | 1/1992 | Kitney et al. |
| 5,193,537 A | 3/1993 | Freeman |
| 5,241,302 A | 8/1993 | Thong |
| 5,247,945 A | 9/1993 | Heinze et al. |
| 5,285,792 A | 2/1994 | Sjoquist et al. |
| 5,330,526 A | 7/1994 | Fincke et al. |
| 5,342,404 A | 8/1994 | Alt et al. |
| 5,348,008 A | 9/1994 | Bornn et al. |
| RE34,800 E | 11/1994 | Hutchins |
| 5,391,187 A | 2/1995 | Freeman |
| 5,409,010 A | 4/1995 | Beach et al. |
| 5,431,685 A | 7/1995 | Alt |
| 5,454,779 A | 10/1995 | Lurie et al. |
| 5,466,244 A | 11/1995 | Morgan |
| 5,472,453 A | 12/1995 | Alt |
| 5,474,574 A | 12/1995 | Payne et al. |
| 5,496,257 A | 3/1996 | Kelly |
| 5,507,778 A | 4/1996 | Freeman |
| 5,511,553 A | 4/1996 | Segalowitz |
| 5,514,079 A | 5/1996 | Dillon |
| 5,533,958 A | 7/1996 | Wilk |
| 5,562,710 A | 10/1996 | Olsen et al. |
| 5,591,213 A | 1/1997 | Morgan |
| 5,611,815 A | 3/1997 | Cole et al. |
| 5,617,853 A | 4/1997 | Morgan |
| 5,619,265 A | 4/1997 | Suzuki et al. |
| 5,645,522 A | 7/1997 | Lurie et al. |
| 5,645,571 A | 7/1997 | Olson et al. |
| 5,662,690 A | 9/1997 | Cole et al. |
| 5,700,281 A | 12/1997 | Brewer et al. |
| 5,735,879 A | 4/1998 | Gliner et al. |
| 5,787,880 A | 8/1998 | Swanson et al. |
| 5,792,190 A | 8/1998 | Olson et al. |
| 5,853,292 A | 12/1998 | Eggert et al. |
| 5,913,685 A | 6/1999 | Hutchins |
| 5,993,398 A | 11/1999 | Alperin |
| 6,021,349 A | 2/2000 | Arand et al. |
| 6,120,442 A | 9/2000 | Hickey |
| 6,125,299 A | 9/2000 | Groenke et al. |
| 6,141,586 A | 10/2000 | Mower |
| 6,155,257 A | 12/2000 | Lurie et al. |
| 6,155,976 A * | 12/2000 | Sackner .............. A47C 21/006 5/600 |
| 6,178,357 B1 | 1/2001 | Gliner et al. |
| 6,185,458 B1 | 2/2001 | Ochs et al. |
| 6,193,519 B1 | 2/2001 | Eggert et al. |
| 6,220,866 B1 | 4/2001 | Amend et al. |
| 6,224,562 B1 | 5/2001 | Lurie et al. |
| 6,238,349 B1 | 5/2001 | Hickey |
| 6,273,728 B1 | 8/2001 | Van Meurs et al. |
| 6,296,490 B1 | 10/2001 | Bowden |
| 6,306,107 B1 | 10/2001 | Myklebust et al. |
| 6,332,872 B1 * | 12/2001 | Young .............. A61H 31/008 601/41 |
| 6,334,070 B1 | 12/2001 | Nova et al. |
| 6,351,671 B1 | 2/2002 | Myklebust et al. |
| 6,356,785 B1 | 3/2002 | Snyder et al. |
| 6,371,765 B1 | 4/2002 | Wall et al. |
| 6,390,996 B1 | 5/2002 | Halperin et al. |
| 6,428,323 B1 | 8/2002 | Pugh |
| 6,443,735 B1 | 9/2002 | Eggert et al. |
| 6,503,087 B1 | 1/2003 | Eggert et al. |
| 6,572,547 B2 | 6/2003 | Miller et al. |
| 6,575,914 B2 | 6/2003 | Rock et al. |
| 6,719,700 B1 | 4/2004 | Willis |
| 6,752,771 B2 | 6/2004 | Rothman et al. |
| 6,758,676 B2 | 7/2004 | Eggert et al. |
| 6,827,695 B2 | 12/2004 | Palazzolo et al. |
| 6,872,080 B2 | 3/2005 | Pastrick et al. |
| 6,961,612 B2 | 11/2005 | Elghazzawi et al. |
| 7,010,344 B2 | 3/2006 | Burnes et al. |
| 7,072,712 B2 | 7/2006 | Kroll et al. |
| 7,074,199 B2 | 7/2006 | Halperin et al. |
| 7,118,542 B2 | 10/2006 | Palazzolo et al. |
| 7,122,007 B2 | 10/2006 | Querfurth |
| 7,122,014 B2 | 10/2006 | Palazzolo et al. |
| 7,164,945 B2 | 1/2007 | Hamilton et al. |
| 7,190,999 B2 | 3/2007 | Geheb et al. |
| 7,192,284 B2 | 3/2007 | Eggert et al. |
| 7,220,235 B2 * | 5/2007 | Geheb .............. A61H 31/007 601/41 |
| 7,245,974 B2 | 7/2007 | Dupelle et al. |
| 7,310,553 B2 | 12/2007 | Freeman |
| RE40,471 E | 8/2008 | Groenke et al. |
| 7,454,244 B2 | 11/2008 | Kassab et al. |
| 7,706,878 B2 | 4/2010 | Freeman |
| 7,761,139 B2 | 7/2010 | Tearney et al. |
| 7,822,470 B2 | 10/2010 | Osypka et al. |
| 7,837,669 B2 | 11/2010 | Dann et al. |
| 7,846,138 B2 | 12/2010 | Dann et al. |
| 8,010,190 B2 | 8/2011 | Olson et al. |
| 8,012,135 B2 | 9/2011 | Dann et al. |
| 8,257,288 B2 | 9/2012 | Hansen et al. |
| 8,317,519 B1 * | 11/2012 | Orlando .............. G09B 23/288 434/262 |
| 8,725,253 B2 | 5/2014 | Johnson et al. |
| 8,876,742 B2 | 11/2014 | Centen |
| 8,939,922 B2 | 1/2015 | Strand et al. |
| 8,994,528 B2 | 3/2015 | Celik-Butler |
| 9,486,390 B2 | 11/2016 | Centen et al. |
| 9,724,266 B2 | 8/2017 | Voss et al. |
| 2001/0011159 A1 | 8/2001 | Cantrell et al. |
| 2001/0018562 A1 | 8/2001 | Sherman et al. |
| 2002/0024888 A1 | 2/2002 | Schreiber |
| 2002/0026131 A1 | 2/2002 | Halperin |
| 2002/0026229 A1 | 2/2002 | Weil et al. |
| 2002/0055694 A1 * | 5/2002 | Halperin .............. A61B 5/742 601/41 |
| 2002/0133197 A1 | 9/2002 | Snyder et al. |
| 2002/0165471 A1 | 11/2002 | Halperin et al. |
| 2002/0193711 A1 | 12/2002 | Halperin et al. |
| 2003/0014055 A1 | 1/2003 | Svadovskiy |
| 2003/0032988 A1 | 2/2003 | Fincke |
| 2003/0055460 A1 | 3/2003 | Owen et al. |
| 2003/0083699 A1 | 5/2003 | Hamilton et al. |
| 2003/0158593 A1 | 8/2003 | Heilman et al. |

(56) References Cited

U.S. PATENT DOCUMENTS

| | | |
|---|---|---|
| 2003/0192547 A1 | 10/2003 | Lurie et al. |
| 2004/0039313 A1 | 2/2004 | Sherman et al. |
| 2004/0039419 A1 | 2/2004 | Stickney et al. |
| 2004/0044374 A1 | 3/2004 | Weinberg et al. |
| 2004/0049118 A1 | 3/2004 | Ideker et al. |
| 2004/0058305 A1 | 3/2004 | Lurie et al. |
| 2004/0082888 A1 | 4/2004 | Palazzolo et al. |
| 2004/0162510 A1 | 8/2004 | Jayne et al. |
| 2004/0162585 A1 | 8/2004 | Elghazzawi et al. |
| 2004/0162586 A1 | 8/2004 | Covey et al. |
| 2004/0162587 A1 | 8/2004 | Hampton et al. |
| 2004/0186525 A1 | 9/2004 | Burnes et al. |
| 2004/0210171 A1 | 10/2004 | Palazzolo et al. |
| 2004/0214148 A1 | 10/2004 | Salvino et al. |
| 2004/0215244 A1* | 10/2004 | Marcovecchio ..... A61B 5/0205 607/5 |
| 2004/0230140 A1 | 11/2004 | Steen |
| 2004/0267324 A1 | 12/2004 | Geheb et al. |
| 2004/0267325 A1 | 12/2004 | Geheb et al. |
| 2005/0101889 A1 | 5/2005 | Freeman et al. |
| 2005/0119706 A1 | 6/2005 | Ideker et al. |
| 2005/0209503 A1 | 9/2005 | Elliott |
| 2005/0256415 A1 | 11/2005 | Tan et al. |
| 2005/0261742 A1 | 11/2005 | Nova et al. |
| 2005/0267536 A1* | 12/2005 | Freeman ............... A61N 1/3925 607/5 |
| 2006/0009809 A1 | 1/2006 | Marcovecchio et al. |
| 2006/0036292 A1 | 2/2006 | Smith et al. |
| 2006/0041278 A1 | 2/2006 | Cohen et al. |
| 2006/0047228 A1* | 3/2006 | Petelenz ............... A61H 31/007 601/44 |
| 2006/0089574 A1 | 4/2006 | Paradis |
| 2006/0116724 A1 | 6/2006 | Snyder |
| 2006/0173500 A1 | 8/2006 | Walker et al. |
| 2006/0174501 A1 | 8/2006 | Harrill |
| 2006/0224053 A1 | 10/2006 | Black et al. |
| 2006/0257377 A1 | 11/2006 | Atala et al. |
| 2006/0270952 A1 | 11/2006 | Freeman et al. |
| 2007/0021788 A1 | 1/2007 | Gazmuri |
| 2007/0054254 A1 | 3/2007 | Pastrick et al. |
| 2007/0060785 A1* | 3/2007 | Freeman ............... A61H 31/006 600/16 |
| 2007/0270724 A1 | 11/2007 | Havardsholm et al. |
| 2007/0276300 A1* | 11/2007 | Olson ................... A61H 31/007 601/41 |
| 2008/0125821 A1 | 5/2008 | Blomquist |
| 2008/0176199 A1 | 7/2008 | Stickney et al. |
| 2008/0300518 A1* | 12/2008 | Bowes ................ A61H 31/005 601/41 |
| 2010/0049266 A1* | 2/2010 | Ochs ................... A61H 31/005 434/265 |
| 2010/0204622 A1* | 8/2010 | Hwang ................ G16H 40/63 601/41 |
| 2010/0221690 A1 | 9/2010 | Freeman et al. |
| 2011/0040217 A1 | 2/2011 | Centen |
| 2011/0201979 A1* | 8/2011 | Voss .................... A61H 31/005 601/41 |
| 2011/0202100 A1* | 8/2011 | Tan .................... A61B 5/14542 607/6 |
| 2011/0301511 A1* | 12/2011 | Freeman .............. A61H 31/005 601/41 |
| 2011/0301513 A1* | 12/2011 | Freeman .............. A61H 31/007 600/509 |
| 2011/0313482 A1* | 12/2011 | Dupelle ............. A61N 1/36031 607/3 |
| 2012/0010543 A1* | 1/2012 | Johnson ................. A61H 31/00 601/41 |
| 2012/0220887 A1 | 8/2012 | Fossan |
| 2012/0226204 A1* | 9/2012 | Coleman ............ A61N 1/37247 601/41 |
| 2013/0018288 A1 | 1/2013 | Jaffe |
| 2013/0023781 A1* | 1/2013 | Freeman .............. A61B 5/0816 601/41 |
| 2013/0226049 A1* | 8/2013 | Kandori ................ A61B 5/103 601/41 |

FOREIGN PATENT DOCUMENTS

| | | |
|---|---|---|
| CN | 1559345 | 1/2005 |
| GB | 2314648 | 1/1998 |
| JP | 2004222785 | 8/2004 |
| WO | 9610984 | 4/1996 |
| WO | 9830282 | 7/1998 |
| WO | 9839061 | 9/1998 |
| WO | 9924114 | 5/1999 |
| WO | 9925306 | 5/1999 |
| WO | 9963926 | 12/1999 |
| WO | 9965560 | 12/1999 |
| WO | 0108629 | 2/2001 |
| WO | 0156652 | 8/2001 |
| WO | 0166182 | 9/2001 |
| WO | 0215836 | 2/2002 |
| WO | 2002072197 | 9/2002 |
| WO | 03009895 | 2/2003 |
| WO | 2004037154 | 5/2004 |
| WO | 2004056303 | 7/2004 |
| WO | 2004073493 | 9/2004 |
| WO | 2004078259 | 9/2004 |
| WO | 2005021089 | 3/2005 |

OTHER PUBLICATIONS

Aase et al., "Compression Depth Estimation for CPR Quality Assessment Using DSP on Accelerometer Signals," IEEE Transactins on Biomedical Engineering, vol. 49, No. 3, Mar. 2002.

Abella et al., Circulation, 2005; 111:428-434.

American Red Cross—Adult CPR/AED Training—Workplace Programs, http://www.redcross.org/hss/cpraed.html, printed from Internet May 14, 1999.

Crit, Care Med. 2000 vol. 28, No. 11 (Suppl.).

Eftestol et al., Circulation, 2000, Predicting Outcome of Defibrillation by Spectral Characterization and Nonparametric Classification of Ventricular Fibrillation in Patients With Out-of-Hospital Cardiac Arrest.

Flewelling, Nellcor Incorporated, Noninvasive Optical Monitoring, Chap. 88, pp. 1346-1353, CRC Press, Inc., 1995.

Force Sensing Resistors—An Overview of the Technology, FSR Integration Guide & Evaluation Parts Catalog with Suggested Electrical Interfaces (no date).

Gruben et al., "System for Mechanical Measurements During Cardiopulmonary Resuscitation in Humans," IEEE Transactions on Biomedical Engineering, vol. 37, No. 2, Feb. 1990.

Heartstream—The Background Behind Our Technology, http://www.heartstream.com/techbk.htm, printed from Internet Jun. 25, 1999.

M.R. Pinsky, Journal of Applied Physiology, vol. 60(2), pp. 604-612, Feb. 1986.

Sato et al., Critical Care Medicine, vol. 25(5), May 1997, pp. 733-736.

Yu et al., Circulation, 2002, Adverse Outcomes of Interrupted Precordial Compression During Automated Defibrillation.

* cited by examiner

| TARGET RATE (COMPRESSIONS/MINUTE) | 1 | 1.5 | 2 | 2.5 |
|---|---|---|---|---|
| 80 | 160 | 240 | 320 | 400 |
| 90 | 180 | 270 | 360 | 450 |
| 100 | 200 | 300 | 400 | 500 |
| 110 | 220 | 330 | 440 | 550 |
| 120 | 240 | 360 | 480 | 600 |
| 130 | 260 | 390 | 520 | 650 |

VELOCITY(INCHES/MINUTE)
(DEPTH (INCHES) X RATE (COMPRESSIONS/MINUTE))

COMPRESSION DEPTH MONITOR WITH VARIABLE RELEASE VELOCITY FEEDBACK

This application is a continuation under 35 U.S.C. § 120 of U.S. patent application Ser. No. 13/874,372, filed on Apr. 30, 2013. All subject matter set forth in the above referenced applications is hereby incorporated by reference in its entirety into the present application as if fully set forth herein.

FIELD OF THE INVENTIONS

The inventions described below relate to the field of CPR.

BACKGROUND OF THE INVENTIONS

Chest compression monitoring during the course of CPR is now possible with the Real CPR Help® and CPR-D-padz technology marketed by ZOLL Medical Corporation. This technology is described in U.S. Pat. No. 6,390,996, 7,108,665, and 7,429,250, and includes the use of an accelerometer to measure accelerations of the chest and calculating the depth of each compression from the acceleration signal. The technology is used in ZOLL's Real CPR Help® compression depth monitoring system to provide real-time rate and depth CPR feedback for manual CPR providers. Commercially, it is implemented in ZOLL's electrode pads, such as the CPR-D•padz® electrode pads. It is also implemented for training use in the PocketCPR® chest compression monitor and PocketCPR® iPhone app.

Halperin, et al., *CPR Chest Compression Monitor*, U.S. Pat. No. 6,390,996 (May 21, 2002), as well as Palazzolo, et al., *Method of Determining Depth of Chest Compressions During CPR*, U.S. Pat. No. 7,122,014 (Oct. 17, 2006), described chest compression monitors capable of determining chest compression depth accurately during repeated rapid chest compressions required by CPR. The devices of Halperin and Palazzolo were adapted to be placed between the CPR provider's hand and the patient's sternum during CPR. In both cases, the CPR chest compression monitor is held in fixed relationship to the chest during use, and the chest compression module is operable to determine the depth of each chest compression based on acceleration data from accelerometers in the chest compression module, without input from other sources, especially without input of data from other sensors fixed in space or remote from the compression module. The disclosures of U.S. Pat. Nos. 6,390,996, 7,108,665, and 7,429,250 to Halperin, and U.S. Pat. No. 7,122,014 to Palazzolo are hereby incorporated by reference.

Geheb, et al., *Method and Apparatus for Enhancement of Compressions During CPR*, U.S. Pat. No. 7,720,235 (May 22, 2007) provides an enhancement a CPR chest compression monitor. In addition to providing feedback regarding depth of compression, this system measures or computes the velocity of the chest compression module, and compare the upward velocity of the chest compression module with a predetermined desired velocity. The system advises, through a display or audio prompt, whether the CPR provider is substantially releasing the chest from compression, or failing to do so. The disclosure of U.S. Pat. No. 7,720,235 is hereby incorporated by reference. Complete release ensures that that the thorax of the CPR victim will expand without hindrance of the CPR provider's weight on the chest, and encourage (or at least avoid hindering) the creation of negative pressure in the chest which encourages venous return and filling of the heart.

The techniques of Halperin, Palazzolo and Geheb are accomplished by various ZOLL defibrillator systems which include and AED box and compression modules (the compression modules are combined with sensing and defibrillating electrodes in a convenient sheet which facilitates proper placement (see FIG. 2). In these systems, a compression monitor which includes accelerometers to sense movement is secured to the patients chest. The CPR provider pushes down on the patient's chest while the compression monitor is trapped between the CPR provider's hands and the patient's chest, so that it generates acceleration signals that correspond to the acceleration of the patient's chest. The AED box includes a control system, a display and speaker, and a defibrillator. The control system (a computer) is programmed to interpret the acceleration signals calculate compression depth and velocity (specifically, release velocity), and generate visual displays and/or audio prompts to be displayed or played to guide the CPR provider. (The control system also analyzes ECG signals obtained from the electrodes, to determine if defibrillating shock should be applied, and may prompt the user to apply shock or automatically operate the defibrillator to apply shock to the patient.) The control system comprises at least one processor and at least one memory including program code with the memory and computer program code configured with the processor to cause the system to perform the functions described throughout this specification.

As currently implemented, the system provides positive or negative feedback regarding release velocity based on a predetermined desirable release velocity of 300 inches (762 cm) per minute, which corresponds to an assumed compression depth of 1.5 inches (38.1 cm).

The threshold of release velocity used to determine whether actual release velocity achieved during CPR is determined through clinical experience, and the systems described above use a single set threshold, programmed into the control system. In some cases, it is desirable to provide greater release velocity, or acceptable to achieve lesser release velocity. For instance, where compression depth achieved is significantly greater than the desired 2 to 2.5 inches (5.08-6.35 cm), it is desirable to release the chest more quickly than is the case for compressions of standard depth, and for compressions of lesser depth, it may be acceptable to release the chest with a lower release velocity.

SUMMARY

The devices and methods described below provide for feedback regarding release velocity of CPR chest compressions based on a user-entered compression depth target or the measured depth of compression. The system may be enhanced in that feedback based on release velocity is based on preconfigured release velocity values corresponding to assumed or desired depth targets, as determined by the CPR provider. For example, the CPR provider may enter a desired target depth of 1.5, 2.0 or 2.5 inches (3.81, 5.08 or 6.35 cm), and the control system will operate to provide feedback which varies according to the selected depth. The CPR compression depth monitoring system, and the method accomplished by the system, may also be enhanced in that feedback based on release velocity is based on the measured depth of compression. The control system is programmed to adaptively determine the depth of compression, or a moving average of depth of compression for a series of compressions, and determine the release velocity of a compression, or a moving average of release velocity for the series of compressions, and determine, based on the actual compression depth, the desired release velocity threshold, and advise the CPR provider with feedback as to whether or not the achieved release velocity meets the release velocity desired for particular depth of compression. The system is adaptive, in the sense that it is programmed to make adjustments in the threshold in response to changes in the actual performance of the chest compression depth and/or rate during the course of CPR on each cardiac arrest victim.

The system can be implemented with accelerometer-based compression monitors, or compression monitors based on other sensing and measuring devices, such a velocity sensors, optical sensors, magnetic sensors, or any other sensor or combination of sensors that provide signals corresponding to movement of the chest (the anterior surface of the thorax) of the CPR victim.

DETAILED DESCRIPTION OF THE INVENTIONS

Figure 1:
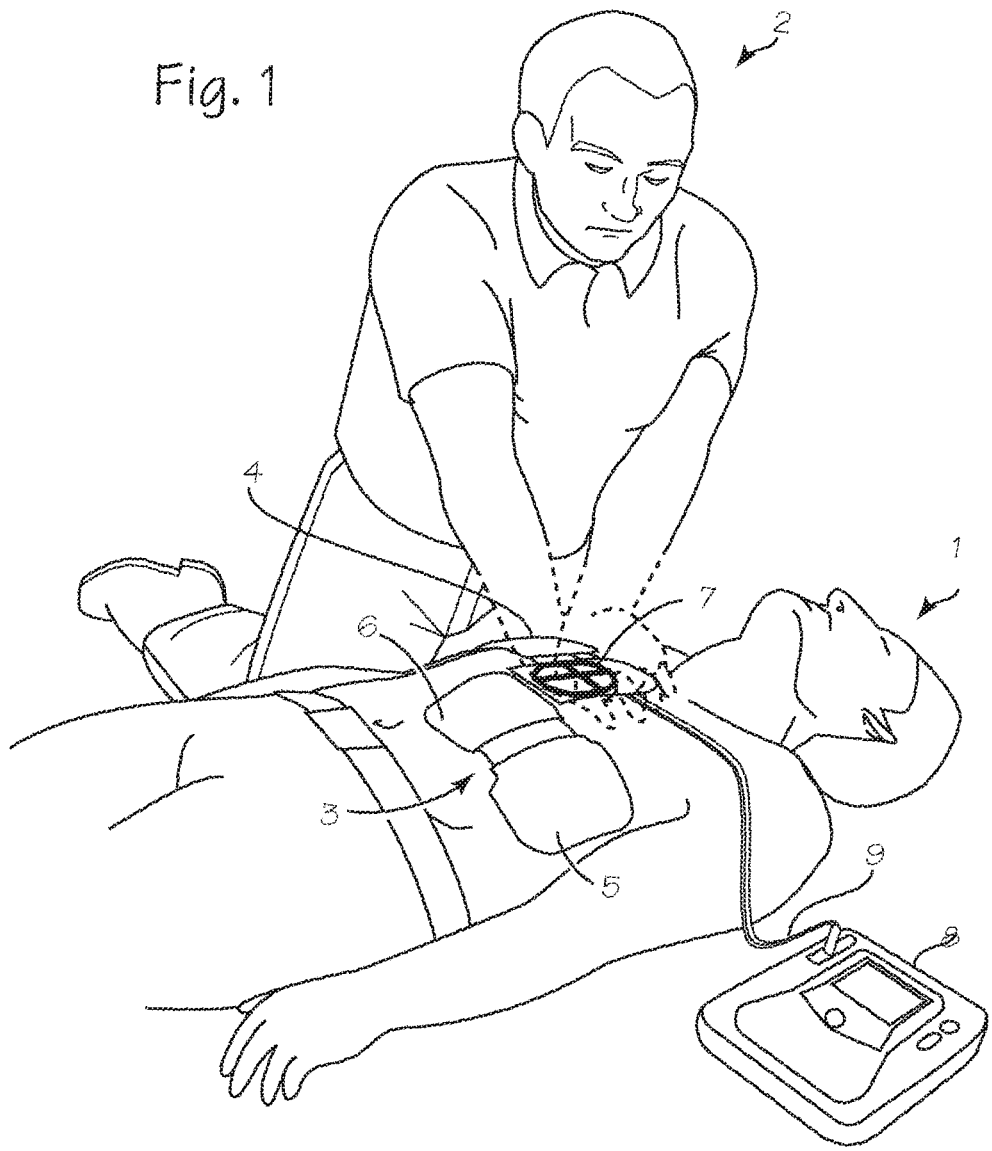
FIG. 1 illustrates the use of a chest compression monitor in use on a patient, with a rescuer providing manual chest compressions.

FIG. 1 illustrates the use of a chest compression monitor in use on a patient 1, with a rescuer 2 providing manual chest compressions. As part of the resuscitation effort, the rescuer has applied an ECG electrode assembly 3 on the patient's chest. This assembly includes a sternum electrode 4, an apex electrode 5, and sternal bridge 6. A chest compression monitor 7 is disposed within the sternal bridge, sandwiched between layers of foam that comprise the bridge. The bridge, along with the cross-hair indicia, serves as a template for proper placement of the chest compression monitor over the sternum of the victim which, together with the configuration of the bridge, ensures that the sternal and apex electrodes are properly placed (for patients of a wide variety of sizes). The electrode assembly is connected to a defibrillator 8 (through cable 9) which is fitted with a control system or systems capable of controlling (and programmed to control) ECG and defibrillating functions and capable of controlling (and programmed to control) the compression monitor functions of interpreting sensor signals (acceleration signals, velocity signals, or distance signals, for example) from the compression monitor, determining the depth of compressions from those sensor signals, and generating and providing feedback to the rescuer. The feedback may be both audio feedback (voice prompts) provided through an annunciator or visual feedback provided on a display. These compression monitor functions can also be accomplished by a control system built into the compression monitor itself, as described in Halperin and as implemented in our PocketCPR® device. The feedback can include prompts to compress more deeply, prompts to compress at a faster or slower rate, and prompts to quickly and completely release the chest of the patient after each compression.

Figure 2:
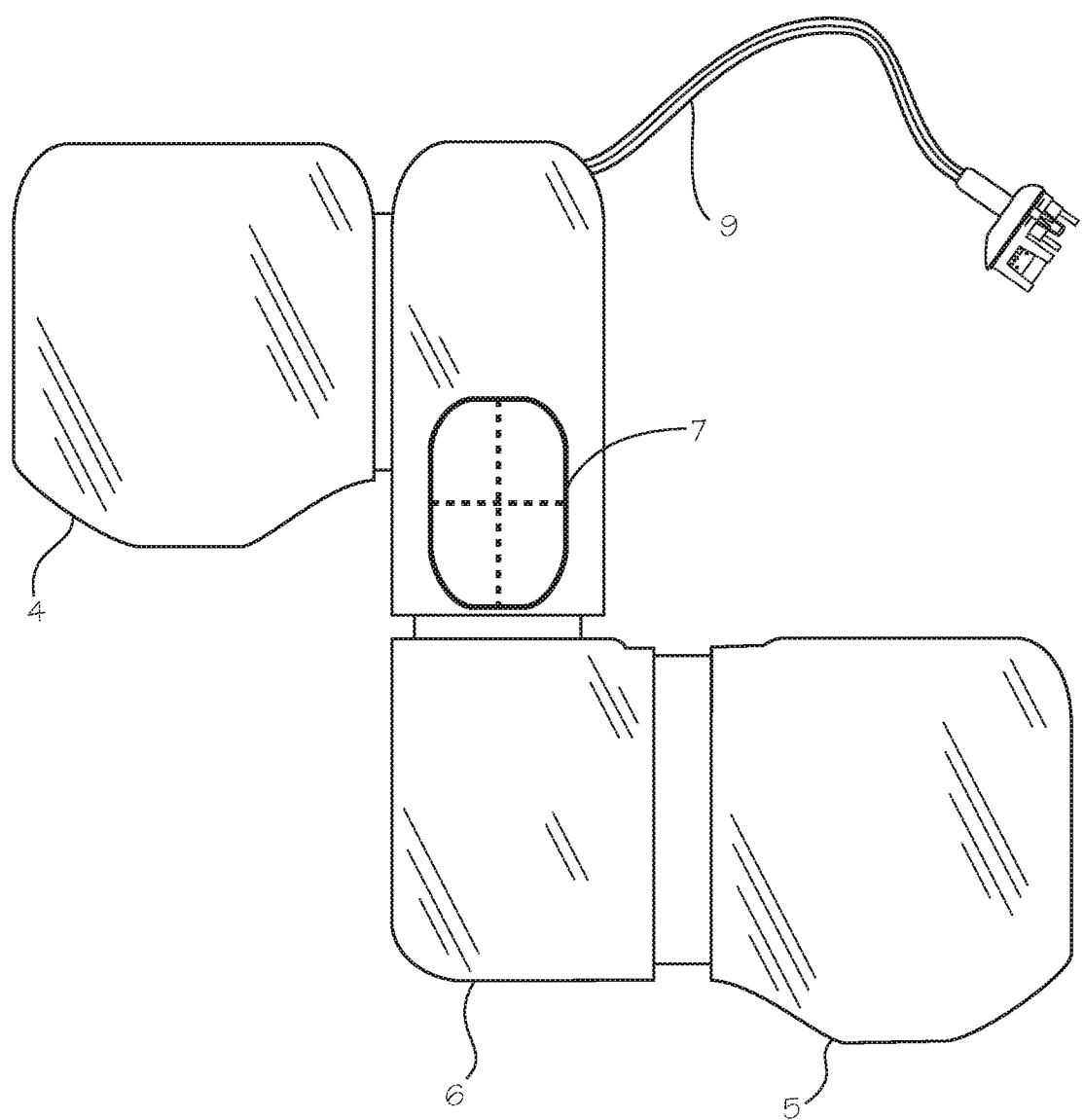
FIG. 2 is a top view of the electrode assembly FIG. 1.

FIG. 2 is a top view of the electrode assembly of FIG. 1, which includes the chest compression monitor 7. In this view, the location of the sternal electrode 4 and apex electrode 5, and the chest compression monitor 7 within the bridge 6 are more clearly shown. The chest compression monitor is disposed within a housing or on an equivalent structure, which itself is disposed within the electrode locating bridge shown in FIG. 1, sandwiched between layers of foam, so that, when applied to the patient, the CPR chest compression monitor is disposed over the sternal notch of the patient. This chest compression monitor and its housing are referred to as a puck in the developing art.

Figure 3:
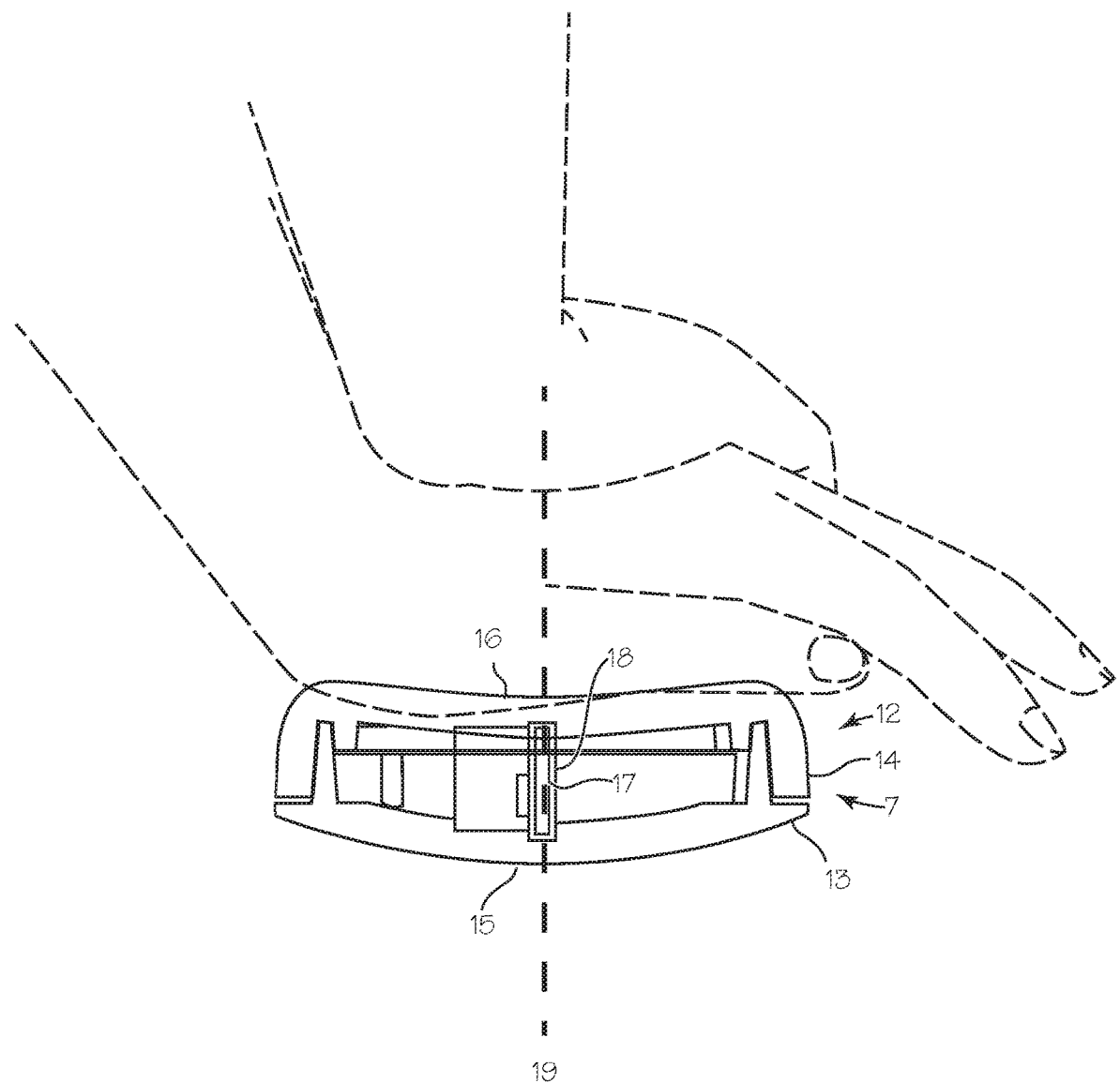
FIG. 3 illustrates the chest compression monitor as implemented in ZOLL Medical's Real CPR Help®chest compression monitor.

FIG. 3 illustrates the chest compression monitor 7 as implemented in ZOLL Medical's Real CPR Help® chest compression monitor and CPR stat padz or CPR-D-padz®. The puck includes a housing 12 with a housing bottom portion 13 and housing top portion 14. The housing bottom portion has a slightly convex bottom surface 15 (which opposes the chest, or anterior surface of the patient's thorax), to conform to the patient's sternal notch. The housing top portion has a slightly concave top surface 16 (superficial, relative to the patient) which facilitates hand placement over the puck during use. The accelerometer assembly 17 that measures acceleration of the puck is disposed in its packaging and on a mounting board 18, within the housing. Typically, the accelerometer assembly is a multi-axis accelerometer assembly, with two or three distinct accelerometers arranged orthogonally to each other, capable of detecting acceleration on two or three orthogonal axes. Preferably, the axes are aligned in the compression monitor to coincide with the compression axis 19 (typically, the vertical axis which corresponds to the anterior/posterior axis of the patient when supine) and one or two axes orthogonal to the compression axis (typically two horizontal axes). With this arrangement, chest compression depth can be measured, as described in the Halperin patents. The accelerometer assembly may also comprise separate accelerometers, with two or three accelerometers rotatably mounted to the housing. As described in Halperin and Palazzolo, the accelerometers produce an acceleration signal corresponding to acceleration of the chest wall achieved during CPR compressions, and the control system processes this acceleration signal to determine compression depth. Also, as described in Geheb, the control system processes this acceleration signal to determine velocity, including the velocity of the chest wall during the period when the CPR provider should be releasing the chest to allow it to expand (the release velocity).

The chest compression monitor, as illustrated in FIGS. 1, 2 and 3, comprises a housing adapted to be held in fixed relation to the chest, specifically the anterior surface of the thorax over the sternum, so that during CPR compressions the movement of the chest compression monitor and sensors of the monitor closely correspond to downward and upward motion of the chest wall of the patient.

The accelerometer-based compression monitor is presented as the most convenient configuration for obtaining information regarding compression depth and release velocity. However, any device operable to sense compression depth and release velocity, or to sense signals or obtain data from which compression depth and release velocity may be derived or determined, may be used in place of the accelerometer based compression monitor. Thus, means for determining release velocity can include the accelerometers described above, velocity sensors which directly measure velocity, and distance sensors of proximity sensors which track the displacement of the compression module. For example, the proximity sensors, including and ultrasonic distance sensor arrangement, optical distance sensors, magnetic motion sensors, RFID sensors and emitter/detector arrangements, for example those described in Freeman and Herken, *Chest Compression Belt with Belt Position Monitoring System,* U.S. Provisional App. 61/654,642 filed Jun. 1, 2012, incorporated herein by reference in its entirety, can be used to measure the actual displacement of the chest, and the control system can readily determine the velocity as the derivative of the displacement curve. Velocity can be measured directly using an imposed magnetic field and inductive sensors, for example, as disclosed in Geheb, by placing a magnet on one side of the thorax (on or under the back of the patient) and an inductive coil on the opposite surface of the thorax (on the chest wall, or anterior surface of the chest) to detect voltage based on induction of current in the coil, which varies with the speed of coil through the magnetic field. A rheostat and mechanical linkage fixed to the puck may used to measure the displacement, as described in Gruben et al., *Sternal Force Displacement Relationship During Cardiopulmonary Resuscitation,* 115 Journal of Biomedical Engineering 195 (May 1993)(which describes the use of mechanical linkages incorporating position sensing transducers to measure chest displacement during CPR), and from displacement data the control system can calculate the release velocity.

Geheb, et al., *Method and Apparatus for Enhancement of Compressions During CPR,* U.S. Pat. No. 7,720,235 (May 22, 2007) and Centen, et al., *Reference Sensor For CPR Feedback Device,* U.S. Pub. 2012/0083720 (Apr. 5, 2012) disclose a system for measuring chest compression depth using a magnetic field generator under the patient and a inductive coil, which senses movement through the magnetic field, as a velocity sensing system. This system can be used as a velocity sensor in the system described above, from which compression depth can be determined. Centen, *Optical Techniques For The Measurement Of Chest Compression Depth And Other Parameters During CPR,* U.S. Pub. 2011/0040217 (Feb. 17, 2011) discloses a system for measuring chest compression depth using infrared optical illumination and detection of the reflected infrared light from the patient. This system can be used as a distance sensor in the system described above, from which velocity of the chest wall movement can be determined.

These and any other means for determining velocity may be used. Also, though a single sensor, and a single type of sensor, are sufficient to provide the necessary information to determine velocity and chest displacement, multiple sensors and sensor types can be used in any permutation. For example, a velocity sensor can be used to directly measure velocity, and an displacement sensor or measurement device (operable independently from the velocity sensor) can be used to directly measure displacement, such that the control system can determine velocity from the velocity sensor and determine displacement from the displacement sensor.

Figure 4:
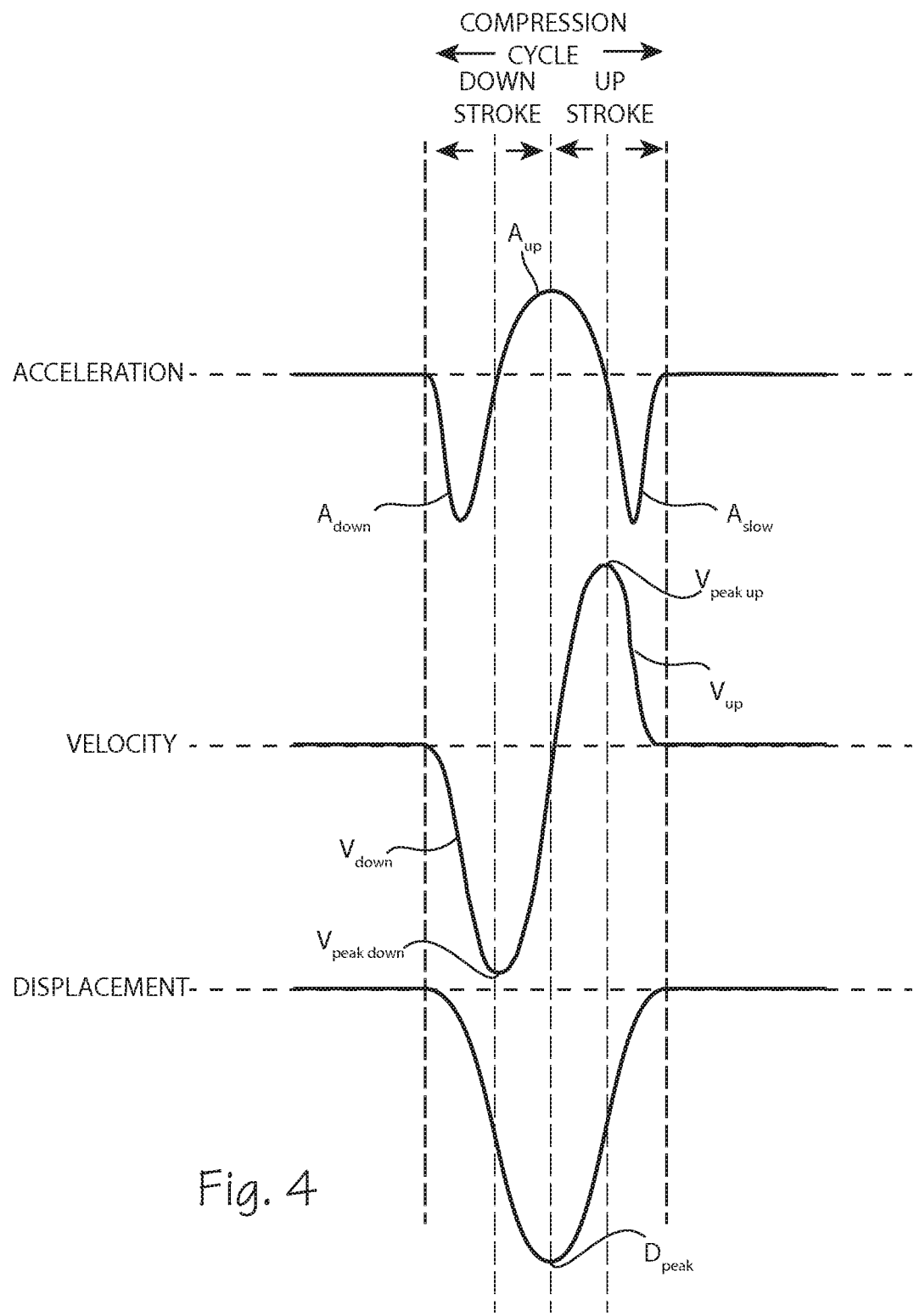
FIG. 4 illustrates the relationship of acceleration, velocity and compression depth for CPR compressions

FIG. 4 illustrates the relationship of acceleration, velocity and compression depth (displacement) for CPR compressions. Any one of these values may be measured, and others may be determined, through straightforward integration or derivation, of the measured signal. As shown in FIG. 4, acceleration, chest wall velocity and chest wall displacement correspond to each other during a compression cycle (a compression cycle includes a downstroke, an upstroke (a release portion), and perhaps some delay between a downstroke and a successive upstroke, or between an upstroke and a successive downstroke). When the CPR provider pushes on the patient's chest, the chest and the compression module held in fixed relation to the chest are accelerated downwardly, experiencing a downward acceleration depicted as a negative acceleration $A_{down}$. Near the end of the downstroke, the acceleration $A_{down}$ slows to zero, and reverses to an upward acceleration $A_{up}$ as the CPR provider releases the compression and natural resilience of the thorax leads to expansion and upward rebound of the chest wall. This is reflected in the positive acceleration $A_{up}$ which quickly slows to zero as the chest reaches its fully expanded position. Upward movement decelerates at $A_{slow}$, and then returns to zero at the completion of the compression cycle. The cycles continue as the CPR provided repeatedly compresses the chest. The velocity curve follows the acceleration curve, with peak downward velocity $V_{peakdown}$ occurring when the downward acceleration $A_{down}$ falls to zero, and upward or release velocity $V_{up}$ increasing while the upward acceleration $A_{up}$ is positive, and $V_{peakup}$ occurring when $A_{up}$ falls to zero. The displacement of the chest reaches its deepest extent $D_{peak}$ when the downward velocity returns to zero, and returns to the original chest position during the period of upward velocity. As these curves are strictly related to each other, each curve can be determined for the others, and data regarding one parameter can be analyzed to determined the other values. The upward velocity, which we refer to as the release velocity, is of primary concern in the inventions described herein, and it can be determined either by directly measuring the velocity (while the valuable displacement data can be determined from the measured velocity), or by measuring acceleration, from which velocity data and displacement data can be determined, or by measuring displacement directly to obtain the valuable chest compression depth measurement and determining release velocity from the displacement data.

Figures 5, 6:
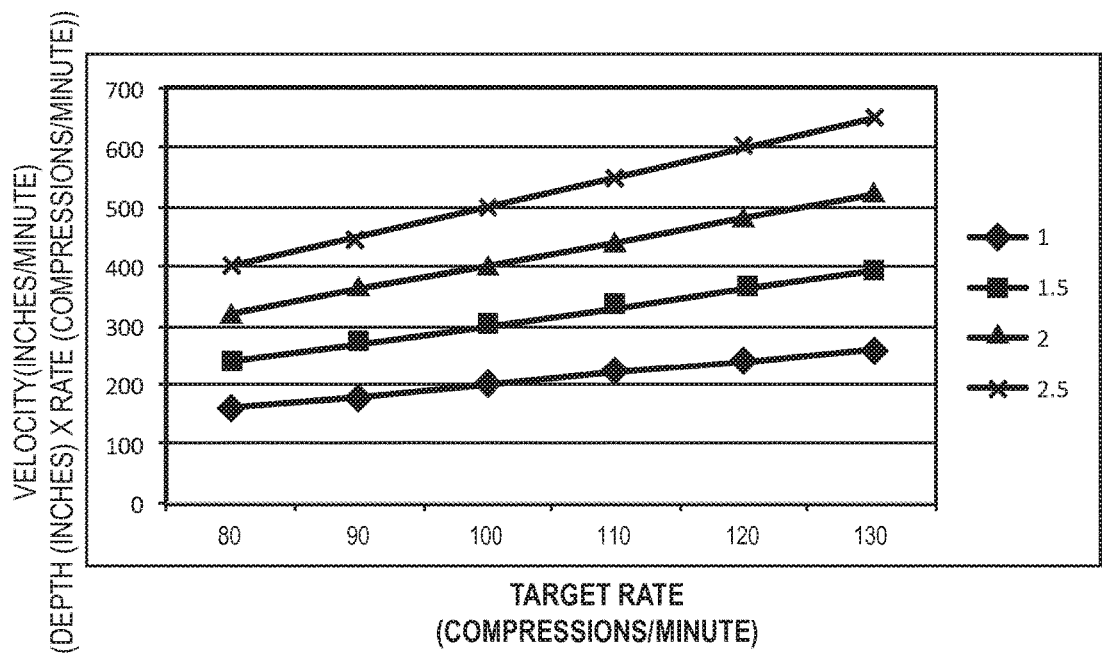
FIG. 5 is a table correlating measured compression depth to desired release velocities.
FIG. 6 is a graph corresponding to the table of FIG. 4.

FIG. 5 is a table correlating measured compression depth to desired release velocities. FIG. 5 indicates the average velocity of the chest wall, and thus the compression module, for various measured compression depths and measured compression rates. For example, in the ideal situation in which compressions are accomplished at the recommended rate of 100 compressions per minute and the recommended depth of 2 inches (5 cm)(on average), the average of the absolute value of the instantaneous velocity of the compression module is 400 inches (1016 cm) per minute. When compression are deeper, such as 3 inches (7.62 cm) per compression, at the same rate, the average instantaneous velocity of the compression module is 600 inches (1524 cm) per minute.

When compressions are accomplished at a more rapid rate, the average instantaneous velocity is greater. So, for example, 2 inch (5.08 cm) compressions at a rate of 120 compression per minute results in a average instantaneous velocity of 440 inches (1016 cm) per minute. Thus the table reflects the average instantaneous velocity of the compression module for compressions at various combinations of depth and rate. The indicated average instantaneous velocities can be taken as minimum upward or "release" velocities of the compression module during the upstroke needed to ensure substantial release of the chest that promotes refilling beneficial to CPR. Accounting for the rapidity of the downstroke, some delay at both the bottom of the compression stroke, and some delay between each complete compression cycle (up and down) and the downward stroke of the next compression, the average instantaneous velocity is a desirable goal for the instantaneous velocity of the upstroke of each compression. The threshold may be adjusted, as clinical experience dictates, to higher or lower velocities. Also, peak velocity during the upstroke may be used as the parameter to be compared to desirable release velocity goals, and velocity during specific period of time during the upstroke (such as the window of time immediately after release (that is, the start of the upstroke, ignoring a portions of the upstroke which is likely to be quite slow (the last few milliseconds, in which the chest wall is nearly fully rebounded, and likely to be moving slowly upwardly)). Where peak release velocity is used to determine the adequacy of release, peak velocities of about 15% to 25% above the average velocities shown in FIG. 5 will be taken as the threshold against which the control system compared measured peak velocity to determine if the chest has been substantially released. Where velocity during a portion of the upstroke is used, average velocity during a small window of time in the upstroke (a window of time that is shorter than the entire release portion) that meets or exceeds a value of about 10% above the average velocities shown in FIG. 5 will be taken as the threshold against which the control system compared measured "window" velocity to determine if the chest has been substantially released. The window may be a period of 50 to 100 milliseconds immediately at the beginning of the upstroke or near the beginning of the upstroke.

FIG. 6 is a graph corresponding to the table of FIG. 5. FIGS. 5 and 6 illustrate a linear relationship between the desired or achieved compression depth and rate and the desired release velocity. However, for some patients, such as elder patients or pediatric or infant patients, the optimal relationship may not be linear, and there may be an upper limit to release velocity based on the resilience of a particular patient, such that the release above a certain threshold may not be possible without active decompression. For such cases, the relationship between compression depth and/or rate and the desired release velocity may be adjusted, such that lower release velocity is considered adequate and feedback is provided based on lower release velocity goals.

In one mode of operation which implements the method insofar as desired release velocity is determined based on the depth of compression and/or the rate of compression, an input means such as a keyboard, selector dial, soft key, or other input can be provided so that the CPR provider or other user can indicate to the control system a desired depth and/or rate of compression for a particular CPR session, and the control system can be programmed to receive and interpret this input and provide release velocity feedback based on this predetermined depth and/or rate. Thus, the system is configurable in the field, at the point of use, by the CPR provider who decides and inputs the optimal configuration based on an individual assessment of the cardiac arrest victim. The desired depth and/or rate is predetermined in the sense that the CPR provider, just prior to the application of CPR compressions, assesses the patient and decides the appropriate depth of compression and/or rate of compression, and inputs this to the control system. In this manner, the release velocity feedback and the chest compression feedback can be provided based on the predetermined depth and rate targets, so that the system can be used to assist in CPR for a wider variety of patients including pediatric patients. For pediatric patients, the depth and rate may vary with the sized of the patient, so that a system that sets the desired release velocity to match the depth chosen by a CPR provider is beneficial. For example, for compression of small children, the chest compression goal is currently 2.5 cm (1 inch) of compression depth. Before providing CPR chest compressions to the child in cardiac arrest, a CPR provider may provide input the control system, indicating that the CPR provider has determined that compressions of 2.5 cm (1 inch), at 100 compressions per minute, are appropriate for this cardiac arrest victim. This is a user-determined chest compression depth and/or rate target. The control system then operates to determine the appropriate release velocity (either by calculation using a formula provided in the software which the control system operates under or by reference to a table of stored values) for the user determined chest compression depth and/or rate. In this mode, the control system is programmed to be user-configured in the field, at the point of use, and is programmed to accept user input regarding desired compression depth and/or rate goals, or accept user input regarding patient age and/or size, and select appropriate release velocity goals, against which it compares the measured release velocity, and provides corresponding output indicating that the CPR provider achieved, or failed to achieve, the desired release velocity. The threshold is chosen by the control system to match the average instantaneous velocity of the compression module necessary to achieve the user-entered compression depth and/or rate. Thus, according to the table, the control system would indicate that the CPR provider has fully released the compression if release velocity meets or exceeds 200 inches (508 cm) per minute, if the user has configured the system for a user-entered goal of 1 inch (2.54 cm) compression, 300 inches (762 cm) per minute for a user-entered goal 1.5 inch (3.8 cm) compression, 400 inches (1016 cm) per minute for a user entered goal of 2 inch (5.08) compression, 500 inches (1270 cm) per minute for a user-entered goal of 2.5 inch (6.35 cm) compression and 600 inches (1524 cm) per minute for a user-entered goal of 3 inch (7.62 cm) compression. The thresholds can be more or less finely granulated. 3 inch (7.62 cm) compression. The thresholds can be more or less finely granulated.

In other modes of operation, the control system is programmed to adaptively determine whether a compression, or a series of compressions, has been fully released based on the depth of the compression, or the series of compressions, rather than on the basis of a predetermined threshold value or a user-configured threshold value. The determined threshold varies with the measured compression depth, and the control system is programmed to choose the threshold, against which it compares the measured release velocity, depending on the measured compression depth, and provide corresponding output indicating that the CPR provider achieved, or failed to achieve, the desired release velocity. This may be accomplished without regard to compression rate. The threshold is chosen by the control system to match the average instantaneous velocity of the compression module necessary to achieve the measured compression depth at a presumed rate (for example, the recommended rate of 100 compressions per minute). Thus, according to the table, the control system would indicate that the CPR provider has fully released the compression if release velocity meets or exceeds 200 inches (508 cm) per minute for a inch (2.54 cm) compression, 300 inches (762 cm) per minute for a 1.5 inch (3.8 cm) compression, 400 inches (1016 cm) per minute for a 2 inch (5.08) compression, 500 inches (1270 cm) per minute for a 2.5 inch (6.35 cm) compression and 600 inches (1524 cm) per minute for a 3 inch (7.62 cm) compression. The thresholds can be more or less finely granulated.

In the user-configurable mode described above, the control system can be programmed to assess the release velocity based on average velocity on the upstroke or release, or the peak velocity detected on the upstroke.

The determined threshold may also vary with the measured compression rate, and the control system is programmed to choose the threshold, against which it compares the measured, depending on the measured compression rate, and provide corresponding output indicating that the CPR provider achieved, or failed to achieve, the desired release velocity. This may be accomplished without regard to compression depth. The threshold is chosen by the control system to match the average instantaneous velocity of the compression module necessary to achieve the measured compression depth at a presumed compression depth (2 inches (5.08 cm), for example). Thus, according to the table, the control system would indicate that the CPR provider has fully released the compression if release velocity meets or exceeds 320 inches (812 cm) per minute for a compression rate of 80 compression per minute, 360 inches (914 cm) per minute for a compression rate of 90 compression per minute, 400 inches (1016 cm) per minute for a compression rate of 100 compression per minute, 440 inches (1118 cm) per minute for a compression rate of 110 compression per minute and so on. The thresholds can be more or less finely granulated.

Both compression depth and compression rate can be taken into account to refine the system described in the preceding paragraphs. As illustrated in the chart of FIG. 4, the velocity threshold can be varied according to both depth and rate of compression. In this case the threshold is chosen by the control system to match the average instantaneous velocity of the compression module necessary to achieve the measured compression depth and compression rate determined by the compression module. The determined threshold varies with both the measured compression depth and the measured compression rate, and the control system is programmed to choose the velocity threshold, against which it compares the measured velocity, depending on the measured compression depth and rate, and provide corresponding output indicating that the CPR provider achieved, or failed to achieve, the desired release velocity. The threshold is chosen by the control system to match the average instantaneous velocity of the compression module necessary to achieve the measured compression depth at a presumed compression depth (2 inches (5 cm), for example).

In each of these three modes, the system is adaptive, in the sense that it is programmed to make adjustments in the threshold in response to changes in the actual performance of the chest compression depth and/or rate during the course of CPR on each cardiac arrest victim. The system adaptively determines the desired threshold for release velocity based on the determined compression depth, the determined compression rate, or a combination of the desired compression depth and compression rate, and applies that adaptively determined threshold to compare with the determined release velocity to determine if the release velocity meets the desired threshold.

In each of the three adaptive modes described above, the control system can be programmed to assess the release velocity based on average velocity on the upstroke or release, or the peak velocity detected on the upstroke.

Figure 7:
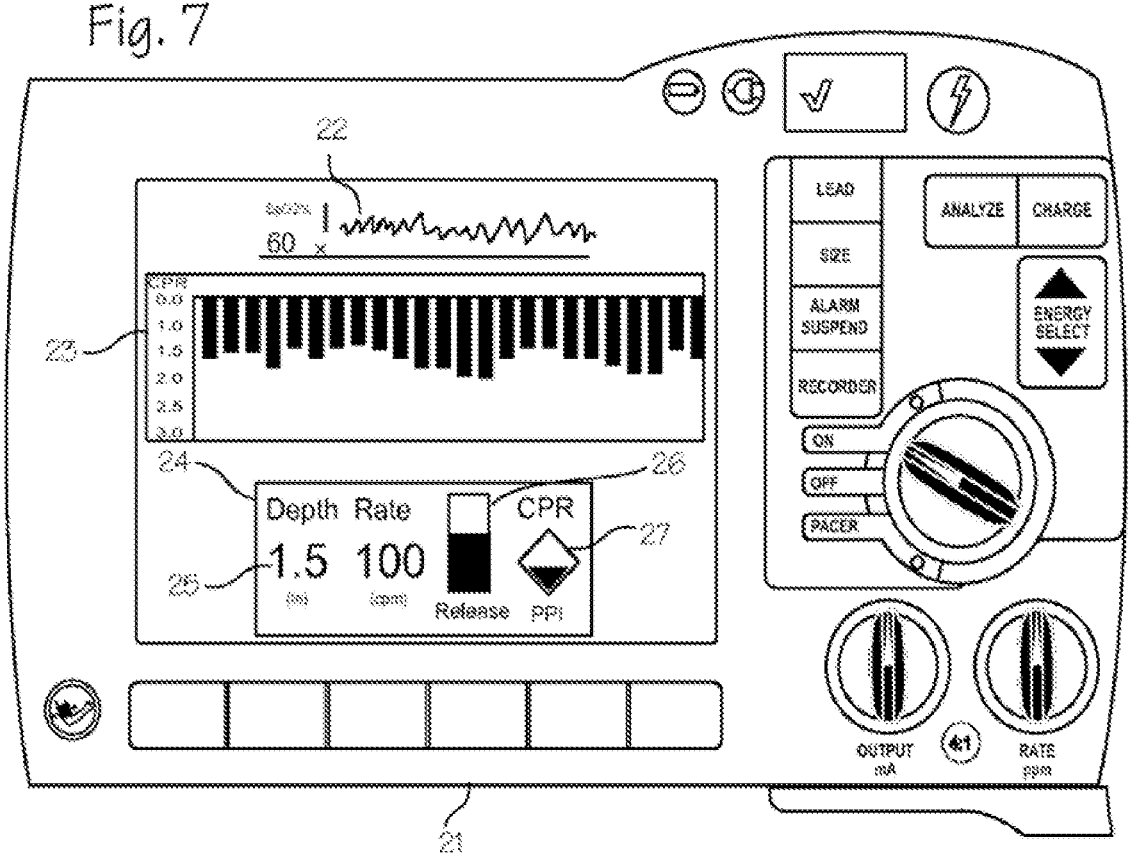
FIGS. 7 and 8 illustrate the output provided by an AED.

FIG. 7 illustrates the output provided by an AED. The control system operates to provide visual output in a portion of display to provide feedback and/or provide prompts to the CPR provider. The display is provided in the front panel of an AED box 21, such as ZOLL's R Series automatic external defibrillator. The AED can accomplish various functions, including ECG monitoring, defibrillation, pacing, and monitoring of other parameters. When used for CPR feedback, the display includes a graph 22 of the CPR victims ECG, a bar graph 23 representing compression depth, a "dashboard" display area 24 for numerical displays 25 of compression depth and compression rate, a progress bar representing release velocity 26, and a diamond shaped icon 27 used to indicate a CPR index, which is determined based on an analysis of both the release velocity and the compression depth. The diamond shaped icon is filled according to an index determined based on rate and depth. We refer to the index as the Perfusion Performance Index. The progress bar representing release velocity, item 26, is referred to as the compression release bar. The control system will operate this display to fill the compression release bar to an extent corresponding to the release velocity determined by the control system from the sensors used to determine release velocity. The control system is programmed to fill the bar completely when it detects release at an upward velocity meeting or exceeding the desired threshold of release velocity, and fill the compression release bar to a proportionately lesser extent when release velocity is slower than the desired threshold. Thus, for example, release velocity of half the desired release velocity will lead to a display in which the compression release bar is half full, and release velocity of 75% of desired release velocity will lead to a display in which the compression release bar is 75% full. In FIG. 7, the compression release bar is only partially filled, indicating that measured release velocity is low compared to the desired threshold, the compression depth is low, hovering around 1.5 inches (3.81 cm) per compression, and the CPR index diamond is only partially filled, indicating inadequate release velocity, poor compression depth, and thus inadequate CPR performance. (Also in FIG. 7, the ECG is indicative of fibrillation, and the blood oxygen level (SpO2%) is very low, as would be expected of a cardiac arrest victim.)

Figure 8:
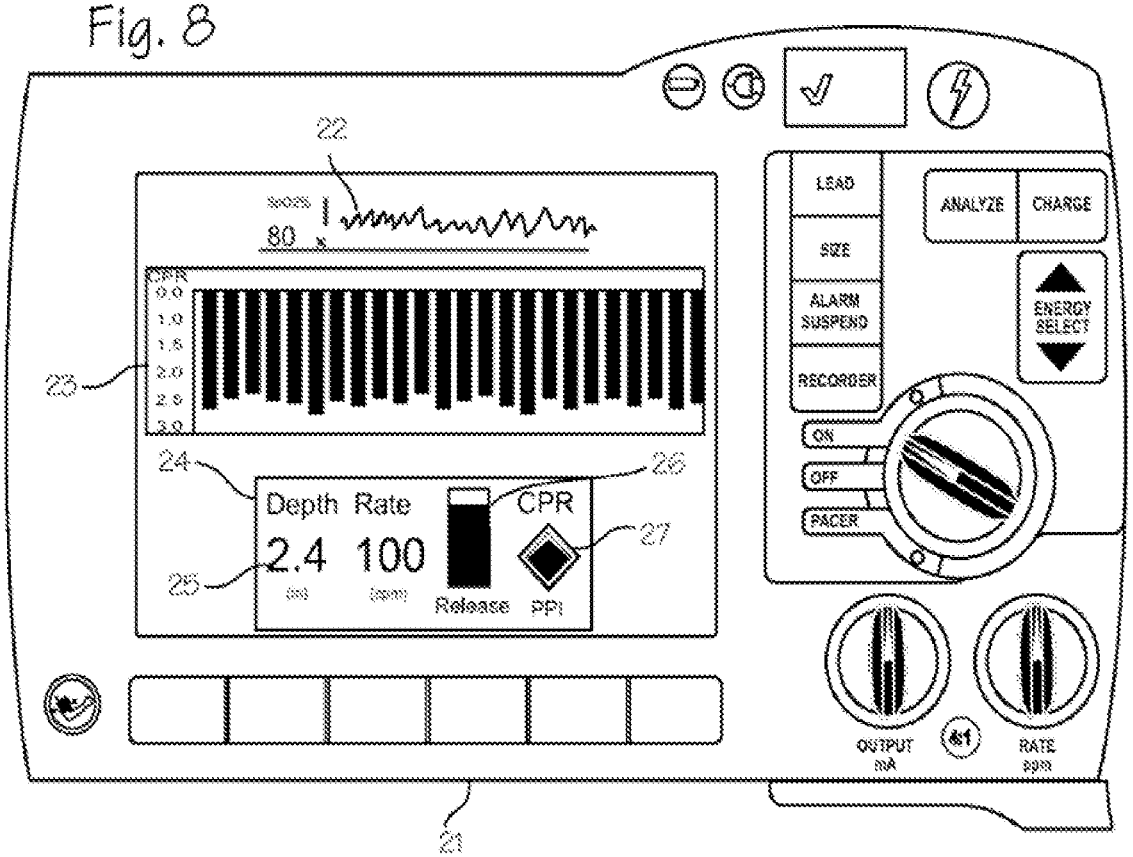

FIG. 8 illustrates the dashboard display area 24 with the display, generated by the control system, to reflect a different state of performance of CPR. In this Figure, the release velocity is improved, vis-à-vis the display of FIG. 7, as shown in the release velocity bar graph 26 and the compression depth over the past several compressions is closer to the ideal of 2-2.5 inches (5.08-6.35 cm), so the diamond shaped icon 27 is more fully filled with a color contrasting that of the background. With the displays of FIGS. 7 and 8, a CPR provider can readily determine from the output of the system that the quality of chest compressions and is good or bad, and can then adjust the effort used to compress the CPR victim or the rapidity of release, until the displays indicate optimal compression depth and release velocity.

Whether release velocity is satisfactory may be determined for each and every compression, or for a series of compressions, or as an average over a series of compressions. When determined on the basis of a series of compressions, the control system tracks a number of compressions, keeping track of those compressions which are fully releases and those compressions that are not fully released. The system designers pre-determine an acceptable compliance rate, and the control system is programmed to issue a prompt and generate the display accordingly. For example, the system may be programmed to track 10 compressions and their associated compression depths and release velocities, and issue a prompt indicated unacceptable release velocity if 2 of the 10 compressions are not fully released (these numbers are, of course, merely exemplary). When determined on the basis of an average over a series of compressions, the system designers pre-determine an acceptable average release velocity, weighted for compression depth, and the control system is programmed to issue a prompt and generate the display accordingly. The control system tracks a number of compressions, keeping track of those compressions and release velocities for each compression. If the average release velocity is less that an acceptable percentage of the desired release velocities, the control system will issue a prompt for more complete release. Alternatively, the control system can average the compression depth, and average the release velocity, and issue a prompt when the average release velocity fall below the threshold for the average compression depth. Thus, it is not necessary to issue a confirmation for every single compression with complete release or a prompt after every single compression with inadequate release.

The diamond-shaped icon 27 provides a quick, overall indicator of how well the rescuer's combined rate and depth of chest compressions match the AHA/ERC recommendations for adult CPR. The CPR Compression Indicator, also known as Perfusion Performance Indicator (PPI), is first displayed as an empty diamond. The control system operates to alter this icon, filling it as compressions begin, and gradually filling it as compressions continues, until consistent chest compression depth exceeding AHA/ERC 2010 guidelines of 2.0 inches (5.08 cm) and rate exceeding 90 compressions per minute (cpm) are achieved simultaneously, at which point the control system completely fills the diamond icon. Should the chest compression rate or depth begin to fall below the configured target levels, the indicator will only partially fill to indicate the need for more rigorous efforts. Following the cessation of compressions, the indicator's fill level gradually decreases until a hollow outline is displayed after a short period of time.

In addition to the visual display, the control system can also be programmed to operate a speaker which provides audio prompt to the CPR provider. For example, when release velocity for a compression or a series of compression is lower than the desired release velocity, the control system can generate a audio prompt such as "Release Fully," and when release velocity is satisfactory, the control system can generate an audio prompts such as "Good Release" or "Good Compression." The audio prompt may be either verbal or non-verbal.

In use, a CPR provider will place the chest compression monitor on the victim's chest, over the victim's sternum. If the chest compression monitor is embedded in an electrode assembly, this will be done by placing the electrode assembly on the chest so that the chest compression monitor is properly located over the sternum. If the chest compression monitor is incorporated into a stand-alone device, such as a puck or a smart phone, this may be done by trapping the device between the CPR provider's hands and the patient's chest. The CPR provider will then press down on the chest, keeping the chest compression monitor between his hands and the victim's chest (or otherwise in fixed relation to the victim's chest), so that the chest compression monitor moves up and down in fixed relation with the patient's chest. The CPR provider will operate an associated control system, and energize the sensors in the chest compression module, to analyze the sensor signals to determine chest compression depth, velocity of the compression monitor (including release velocity), and, optionally, the rate of compression, and determine the desired release velocity based on the determined chest compression depth (and, optionally, the chest compression rate), compare the determined release velocity to the desired release velocity, and operate an output device to provide prompts indicating whether the release velocity meets or fails meet the desired release velocity (and whether the chest compression depth meets the desired chest compression depth). If the system is used in a user-configurable mode, the CPR provider will operate an associated control system, and energize the sensors in the chest compression module, to analyze the sensor signals to determine chest compression depth, velocity of the compression monitor (including release velocity), and, optionally, the rate of compression, and determine the desired release velocity based on the user-entered chest compression depth target (and, optionally, the chest compression rate)(or the user-entered patient information), compare the determined release velocity to the desired release velocity, and operate an output device to provide prompts indicating whether the release velocity meets or fails meet the desired release velocity (and whether the chest compression depth meets the desired chest compression depth).

Thus, the system is used in a method for facilitating the effective administration of cardiopulmonary resuscitation (CPR). The method includes operating a sensor for generating a signal corresponding to motion of a cardiac arrest victim's chest to determine motion of the cardiac arrest victim's chest during CPR chest compressions, in tandem with operating a control system with an output device to provide prompts in response to the motion signals. The control system is operable to receive a signal corresponding to motion of the chest, and programmed to determine the depth of compressions from a signal corresponding to motion of the chest, and determine release velocity during a release portion of a CPR compression cycle from a signal corresponding to motion of the chest, and programed to determine whether the CPR provider is substantially releasing the chest following chest compressions, and further programmed to operate the output device to provide the CPR provider with information as to whether the chest is being substantially released following chest compressions. Specifically, the control system is programmed to determine whether the CPR provider has substantially released the chest based on a desired release velocity threshold, which it is programmed to determine based on (1) the CPR provider's target chest compression depth and/or compression rate, as entered by the operator or (2) the actual depth of compression and/or compression rate as measured by the sensors. The control system then provides, through the output device, a prompt to the CPR provider whether the chest is being substantially released following chest compressions. As the CPR provider performs CPR chest compressions on the patient, with the goal of meeting approved standards of depth, rate and release velocity, the CPR provider monitors the outputs, occasionally viewing the output displays and listening to audio prompts as the are provided by the system, and adjusts the effort of chest compression if the output indicates that depth, rate, or release velocity differs from the desired thresholds.

While the preferred embodiments of the devices and methods have been described in reference to the environment in which they were developed, they are merely illustrative of the principles of the inventions. The elements of the various embodiments may be incorporated into each of the other species to obtain the benefits of those elements in combination with such other species, and the various beneficial features may be employed in embodiments alone or in combination with each other. Other embodiments and configurations may be devised without departing from the spirit of the inventions and the scope of the appended claims.

I claim:

1. A system for providing cardiopulmonary resuscitation (CPR) feedback configurable at a point of use, the system comprising:

one or more sensors configured to generate a signal corresponding to motion of a chest of a patient during an administration of manual chest compressions by a rescuer;

defibrillation electrodes; and a defibrillator configured to couple to the one or more sensors and the defibrillation electrodes, the defibrillator comprising:
- a user input separate from the defibrillation electrodes and configured to provide input signals to a control system, wherein the input signals are indicative of a pre-determined compression depth goal for the manual chest compressions that comprises an indication of a rescuer assessment of whether the patient is an adult patient or a pediatric patient,
- the control system comprising one or more processors and a memory, the one or more processors configured to
  - determine a goal for release velocity for the manual chest compressions based on the provided input signals, and
  - determine chest compression feedback that varies based on the input signals to the control system indicative of the pre-determined compression depth goal for the manual chest compressions that comprises an indication of a rescuer assessment of whether the patient is an adult patient or a pediatric patient and is based at least in part on the motion of the chest during the administration of the manual chest compressions, wherein the chest compression feedback guides the rescuer in performing the manual chest compressions in accordance with the pre-determined compression depth goal and the determined goal for release velocity, and
  - a display configured to display the chest compression feedback.

2. The system of claim 1 wherein the defibrillator is an automated external defibrillator.

3. The system of claim 1 wherein the input signals to the control system indicative of the pre-determined compression depth goal for the manual chest compressions indicates a 1.5 inch (3.8 cm) compression depth goal.

4. The system of claim 1 wherein the input signals to the control system indicative of the pre-determined compression depth goal for the manual chest compressions indicates a 2 inch (5.08 cm) compression depth goal.

5. The system of claim 1 wherein the chest compression feedback is indicative of a first comparison between the motion of the chest as indicated by the signal from the one or more sensors and at least the pre-determined compression depth goal and of a second comparison between the motion of the chest as indicated by the signal from the one or more sensors and the determined goal for release velocity.

6. The system of claim 5 wherein the display is configured to display the chest compression feedback as a graphical indication of the first comparison and the second comparison.

7. The system of claim 6 wherein the chest compression feedback indicates whether the rescuer achieved or failed to achieve the pre-determined compression depth goal and whether the rescuer achieved or failed to achieve the determine goal for release velocity.

8. The system of claim 1 wherein the chest compression feedback further comprises compression rate feedback based on the motion of the chest as indicated by the signal from the one or more sensors and a chest compression rate goal.

9. The system of claim 8, wherein the pre-determined compression depth goal and the compression rate goal correspond to one or more of American Heart Association and European Resuscitation Council CPR guidelines.

10. The system of claim 1, wherein the chest compression feedback comprises a graphic icon that fills partially or fully with a color contrasting a background based on the signal from the one or more sensors.

11. The system of claim 1 wherein the chest compression feedback is numeric feedback.

12. The system of claim 1, wherein the release velocity comprises a peak release velocity during release of a portion of the manual chest compressions.

13. The system of claim 1, wherein the chest compression feedback comprises an indication of a measured value for release velocity for a manual chest compression being performed of the manual chest compressions and at least one instruction to guide the rescuer in performing the manual chest compressions in accordance with the pre-determined compression depth goal and the determined goal for release velocity.

14. The system of claim 13, wherein the indication of the measured value for release velocity comprises a graphical progress bar that fills by an amount determined based on a comparison between the measured value for release velocity and the determined goal for release velocity.

15. The system of claim 1, wherein the input signals provided by the user input comprise an input value for the pre-determined compression depth goal, which is within a range of potential chest compression depths suitable for treatment of one of an adult patient or a pediatric patient, and wherein the goal for release velocity is based on the input value for the pre-determined compression depth goal and the indication of the rescuer assessment of whether the patient is an adult patient or a pediatric patient.

* * * * *

UNITED STATES PATENT AND TRADEMARK OFFICE
CERTIFICATE OF CORRECTION

| | |
|---|---|
| PATENT NO. | : 11,944,582 B2 |
| APPLICATION NO. | : 16/167573 |
| DATED | : April 2, 2024 |
| INVENTOR(S) | : Guy R. Johnson |

It is certified that error appears in the above-identified patent and that said Letters Patent is hereby corrected as shown below:

In the Claims

Column 14, Lines 10-11, Claim 7, delete "determine" and insert -- determined --

Signed and Sealed this
Twenty-eighth Day of May, 2024

*Katherine Kelly Vidal*

Katherine Kelly Vidal
*Director of the United States Patent and Trademark Office*